United States Patent
Höfgen et al.

(10) Patent No.: US 7,169,787 B2
(45) Date of Patent: Jan. 30, 2007

(54) 7-AZAINDOLES, USE THEREOF AS PHOSPHODIESTERASE 4 INHIBITORS AND METHOD FOR PRODUCING THE SAME

(75) Inventors: Norbert Höfgen, Ottendorf-Okrilla (DE); Ute Egerland, Radebeul (DE); Thomas Kronbach, Radebeul (DE); Degenhard Marx, Radolfzell (DE); Stefan Szelenyi, Schwaig (DE); Hildegard Kuss, Dresden (DE); Emmanuel Polymeropoulos, Frankfurt (DE)

(73) Assignee: Elbion AG, Radebeul (DE)

( * ) Notice: Subject to any disclaimer, the term of this patent is extended or adjusted under 35 U.S.C. 154(b) by 254 days.

(21) Appl. No.: 10/399,051

(22) PCT Filed: Oct. 25, 2001

(86) PCT No.: PCT/EP01/12376

§ 371 (c)(1),
(2), (4) Date: Jun. 17, 2003

(87) PCT Pub. No.: WO02/34747

PCT Pub. Date: May 2, 2002

(65) Prior Publication Data

US 2004/0106641 A1    Jun. 3, 2004

Related U.S. Application Data

(60) Provisional application No. 60/244,342, filed on Oct. 30, 2000.

(30) Foreign Application Priority Data

Oct. 27, 2000  (DE) .............................. 100 53 275

(51) Int. Cl.
  A61K 31/437   (2006.01)
  A61K 31/5377  (2006.01)
  C07D 295/02   (2006.01)
  C07D 221/04   (2006.01)
  C07D 221/02   (2006.01)

(52) U.S. Cl. ................ 514/253.04; 544/238; 544/127; 514/300; 514/235.5; 546/113

(58) Field of Classification Search ............. 546/113; 544/61, 127, 310, 362; 514/300, 274, 234.5, 514/228.2, 253.04
See application file for complete search history.

(56) References Cited

U.S. PATENT DOCUMENTS 5,023,265 A   6/1991  Scherlock et al.
5,464,861 A  11/1995  Dobrusin et al.
5,811,432 A   9/1998  Marfat et al.

FOREIGN PATENT DOCUMENTS

| GB | 1 141 949 A | 2/1969 |
|---|---|---|
| JP | 09221423 | 8/1987 |
| JP | 06247966 A * | 9/1994 |
| JP | 09169665 | 6/1997 |
| JP | 10 120681 A | 5/1998 |
| WO | WO-91/09598 | 7/1991 |
| WO | WO-94/02465 | 2/1994 |
| WO | WO-94/03427 | 2/1994 |
| WO | WO-95/28926 | 11/1995 |
| WO | WO-96/11929 | 4/1996 |
| WO | WO-96 11929 A | 4/1996 |
| WO | WO-96/31476 | 10/1996 |

OTHER PUBLICATIONS

Burnouf C. Annual Reports in Medicinal Chemistry, 1998, Academic Press, Chapter 10, pp. 91-109.*
Giembycz, Mark A., "Cilomilast: a second generation phosphoiesterase 4 inhibitor for asthma and chronic obstructive pulmonary disease", Expert Opinion Investig. Drugs (2002) 10(7):1361-1379.*
Patent Abstracts of Japan, JP 04021681 dated Jan. 24, 1992.
Tyrosine Kinase Inhibitors, , Rewcastle, et al.. J. Med. Chem. 1994.
Corticotropin-Releasing Hormone . . . Studies, Hodge, et al. J. Med. Chem. 1999.
New 5-HT$_3$ (Serotonin-3) Receptor, IV Synthesis and Structure., Kato, et al. Chem. Pharm. Bull. 43, (8) 1995.
Palfreyman, et al. "Phosphodiesterase Type IV Inhibitors" Progress in Medicinal Chemistry- vol. 33 (1996).
Miyamoto, et al., "Reduction of Bone Loss by Denbufylline, an Inhibitor of Phosphodiesterase 4", Biochemical Pharmacology, vol. 54 (1997).
Hanifin, et al. "Monocyte Phosphodiesterase Abnormalities and Dysregulation of Lymphocyte Function in Atopic Dermatitis", The Society for Investigative Dermatology, Inc. vol. 105. (1995).
Cavalla, et al., "Phosphodiesterase IV Inhibitors: Structural Diversity and Therapeutic Potential in Asthma", Current Medicinal Chemistry (1995).
Palfreyman, "Phosphodiesterase type IV Inhibitors as anti-inflammatory agents", Drugs of the Future (1995).
Karlsson, et al. "Pulmonary-Allergy, Dermatological, Gastrointestinal & Arthritis, Phosphodiesterase 4 inhibitors for the treatment of asthma", (1997).
Palacios, et al., "Second Messenger Systems as Targets for New Therapeutic Agents: Focus on Selective Phosphodiesterase Inhibitors", Il Farmaco, 50 (1995).

* cited by examiner

*Primary Examiner*—Cecilia Tsang
*Assistant Examiner*—Lexington A. Hoffman
(74) *Attorney, Agent, or Firm*—Fulbright & Jaworski L.L.P.

(57) ABSTRACT

The invention relates to new 7-azaindoles, their use as inhibitors of phosphodiesterase 4 and to methods for their synthesis.

11 Claims, No Drawings

7-AZAINDOLES, USE THEREOF AS PHOSPHODIESTERASE 4 INHIBITORS AND METHOD FOR PRODUCING THE SAME

This application is a §371 of PCT/EP01/12376 filed Oct. 25, 2001 and claims priority from DE 100 53 275.6 filed Oct. 27, 2000 and also claims priority under 35 U.S.C. §119 from U.S. Provisional Application No. 60/244,342 filed Oct. 30, 2000.

TECHNICAL FIELD

The invention relates to substituted 7-azaindoles of the general formula 1

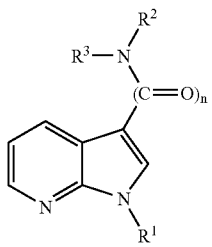

methods for their synthesis, pharmaceutical preparations, which contain these compounds, as well as the pharmaceutical use of these compounds, which are inhibitors of phosphodiesterase 4, as active ingredients for the treatment of diseases, which can be affected with an inhibition of phosphodiesterase 4 activity in immunocompetent cells (such as macrophages and lymphocytes) by the inventive compounds.

PRIOR ART

The activation of receptors of the cell membrane by transmitters leads to the activation of the "second messenger" system. The adenylate cyclase synthesizes the active, cyclic AMP (cAMP) or cyclic GMP (cGMP) from AMP and GMP. These lead, for example, to relaxation in smooth muscle cells or to the inhibition of the release or synthesis of the mediator in inflammation cells. The "second messenger" cAMP and cGMP is broken down by the phosphodiesterases (PDE). Up to the present, 11 families of PDE enzymes (PDE1 to PDE11) are known, which differ due to their substrate specificity (cAMP, cGMP or both) and the dependence on other substrates (such as calmodulin). These isoenzymes have different functions in the body and are differently pronounced in the individual types of cells (Beavo, J. A., M. Conti and R. J. Heaslip, Multiple cyclic nucleotide phosphodiesterases. Mol. Pharmacol. 1994, 46:399–405: Hall, I. P., Isoenzyme selective phosphodiesterase inhibitors: potential clinical uses, Br. J. clin. Pharmacol 1993, 35:1–7). The inhibition of the different PDE isoenzyme types results in an accumulation of cAMP and/or cGMP in the cells, which can be used therapeutically (Torphy, T. J., G. P. Livi, S. B. Christensen, Novel Phosphodiesterase Inhibitors for the Therapy of Asthma, Drug News and Perspectives 1993, 6:203–214).

In the cells important for allergic inflammations (lymphocytes, mast cells, eosinophilic granulocytes, macrophages), the predominant PDE isoenzyme is type 4 (Torphy, J. T. and B. J. Undem, Phophordiesterase inhibitors: new opportunities for the treatment of asthma. Thorax 1991, 46:512–523). The inhibition of the PDE 4 by suitable inhibitors is therefore regarded as an important start for the treatment of a plurality of allergy-induced illnesses (Schudt, Ch., G. Dent and K. Rabe, Phosphodiesterase Inhibitors, Academic Press London 1996).

An important property of phosphodiesterase 4 inhibitors is the inhibition of the release of tumor necrosis factor α (TNFα) from inflammation cells. TNFα is an important pro-inflammatory cytokin, which affects a plurality of biological processes. TNFα is released, for example, from activated macrophages, activated T lymphocytes, mast cells, basophils, fibroblasts, endothelium cells and astrocytes in the brain. It has itself an activating effect on neutrophils, eosinophils, fibroblasts and endothelium cells, as a result of which different tissue-destroying mediators are released. In monocytes, macrophages and T lymphocytes, TNFα brings about the increased production of further pro-inflammatory cytokines such as GM-CSF (granulocy-macrophage colony-stimulating factor) or interleukin-8. Because of its inflammation-promoting and catabolic effect, TNFα plays a central role in a plurality of illnesses, such as the inflammations of respiratory pathways, inflammations of the joints, endotoxic shock, tissue rejections, AIDS and numerous other immunological diseases. Accordingly, inhibitors of phosphodiesterase 4 are also suitable for the treatment of such illnesses, which are associated with TNFα.

Chronic obstructive pulmonary diseases (COPD) are widespread in the population and also have a great economic importance. For example, COPD diseases are responsible for approximately 10 to 15% of the costs of all illnesses in the developed countries and about 25% of all deaths in the USA are attributable to this cause (Norman, P.: COPD: New developments and therapeutic opportunities, Drug News Perspect. 11 (7), 431–437, 1998); however, at the time of death, most patients are older than 55 years (Nolte, D.: Chronic Bronchitis—a National Disease of Multifactorial Origin. Atemw.-Lungenkrkh. 20 (5), 260–267, 1994). The WHO estimates that, within the next 20 years, COPD will be the third most frequent cause of death.

The syndrome of chronic, obstructive pulmonary diseases (COPD) combines different syndromes of chronic bronchitides with the symptoms of productive coughing and progressive and irreversible deterioration of the lung function (the expiration is particularly affected). The course of the disease is episodal and complicated frequently by bacterial infections (Rennard, S. I.: COPD: Overview of definitions, Epidemiology, and factors influencing its development. Chest, 113 (4) Suppl. 235S–241S, 1998). In the course of the disease, the lung function decreases steadily, the lung increasingly becomes emphysematic and the respiratory distress of the patients is obvious. This illness clearly impairs the quality of life of the patients (shortness of breath, a low exercise tolerance) and significantly shortens their life expectancy. Aside from environmental factors, the main risk factors are smoking (Kummer, F.: Asthma and COPD, Atemw.-Lungenkrkh. 20 (5), 299–302, 1994; Rennard S. I.: COPD: Overview of definitions, Epidemiology, and factors influencing its development. Chest, 113 (4) Suppl., 235S–241S, 1998) and men are therefore affected more frequently than are women. This picture will change in the future due to changing habits and the increasing number of women, who smoke.

The present treatment aims only at relieving the symptoms, without intervening into the causes of the progression of the disease. The use of longer acting beta2 agonists (such as Salmeterol), possibly in combination with muscarinergic antagonists (such as Ipratropium) improves the lung function by bronchial dilation and is used routinely (Norman, P.: COPD: New developments and therapeutic opportunities, Drug News Perspect. 11 (7), 431–437, 1998). Bacterial infections, which must be treated with antibiotics, play a large role in COPD episodes (Wilson, R.: The role of infections in COPD, Chest, 113 (4) Suppl., 242S–248S, 1998, Grossman, R. F.: The value of antibiotics and the outcomes of antibiotic therapy in exacerbations of COPD, Chest, 113 (4) Suppl., 249S–255S, 1998). The treatment of this disease is still unsatisfactory, particularly with respect to the continuous decrease in lung function. New treatment approaches, which attack the inflammation mediators, proteases or adhesion molecules, could be very promising (Barnes, P. J.: Chronic obstructive disease: new opportunities for drug development, TiPS. 10 (19), 415–423, 1998).

Independently of the bacterial infections complicating the disease, a chronic inflammation, which is dominated by neutrophil granulocytes, is found in the bronchi. Among others, the mediators and enzymes, released by neutrophil granulocytes, are made responsible for the structural changes observed in the respiratory tract (emphysema). The inhibition of the activity of the neutrophil granulocytes thus is a rational starting point for preventing or retarding progress of the COPD (deterioration of the lung function parameters). An important stimulus for the activation of the granulocytes is the pro-inflammatory cytokin TNFα (tumor necrosis factor). For example, it is known that TNFα stimulates the formation of free oxygen radicals by neutrophil granulocytes (Jersmann, H. P. A., D. A. Rathjen and A. Ferrante: Enhancement of LPS-induced neutrophil oxygen radical production by TNFα, Infection and Immunity, 4, 1744–1747, 1998). PDE4 inhibitors can inhibit very effectively the release of TNFα from a plurality of cells and thus suppress the activity of the neutrophil granulocytes. The nonspecific PDE inhibitor, pentoxifylline, is in a position to inhibit the formation of oxygen radicals as well as the phagocytic ability of neutrophil granulocytes (Wenisch, C., K. Zedtwitz-Liebenstein, B. Parschalk and W. Graninger: Effect of pentoxifylline in vitro on neutrophil reactive oxygen production and phagocytic ability, assessed by flow cytometry, Clin. Drug Invest., 13(2): 99–104, 1997).

Different PDE 4 inhibitors are already known. Predominantly, these are xanthine derivatives, rolipram analogs or nitraquazone derivatives (survey in Karlsson, J.-A. and D. Aldos, Phosphodiesterase 4 inhibitors for the treatment of asthma, Exp. Opin. Ther. Patents 1997, 7: 989–1003). Until now, it has not been possible to bring any of these compounds to the stage of a clinical application. It had to be noted that the known PDE 4 inhibitors also have various side effects, such as nausea and emesis; up till now, it has not been possible to suppress these adequately. For this reason, the discovery of new PDE 4 inhibitors with a better therapeutic range is necessary.

The use of 7-azaindoles for the development of new active ingredients for different indications has so far been described only in relatively few cases.

In the Japanese patent JP 10120681 (Fujisawa Pharmaceutical Co., Ltd.) 5- and 7-azaindoles of the general formula

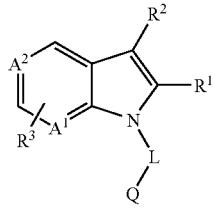

are claimed, in which $R^1$ can represent hydrogen or short alkyl groups, $R^2$ can represent hydrogen, halogen, short alkyl groups, cycloalkyl groups, alkylcarbonyl groups or alkanoyl groups, $R^3$ represents alkanoyl groups, protected carboxylic acid groups, the cyano group or substituted carbamoyl groups. L represents a short alkylene bridge. Q represents substituted aromatic and heterocyclic groups. Of $A^1$ and $A^2$, one represents nitrogen and the other CH. These compounds differ from the inventive compounds particularly with respect to the substituents $R^2$ and $R^3$ and partially with respect to $R^1$ and $A^2$. The compounds described are claimed as inhibitors of a cGMP specific phosphodiesterase (PDE 5). Various cardiac circulation diseases, bronchitis, asthma, rhinitis, impotence, complications of diabetes and glaucoma are named as areas of application.

The synthesis of various 3-aminoalkyl-4-azaindoles and 3-aminoalkyl-7-azaindoles is described by L. N. Yakhontov, S. S. Liberman, D. M. Krasnokutskaya et al. in Khim.-Farm. Zh. 8 (11), 1974, 5–9. For the 3-(2-aminoethyl)-7-azaindoles, a depressive or antidepressive effect is described. A blood pressure-lowering effect was noted for 3-aminomethyl-7-azaindoles.

A. J. Verbiscar, in J. Med. Chem. 15 (2), 1972, 149–152 describes the compound of formula

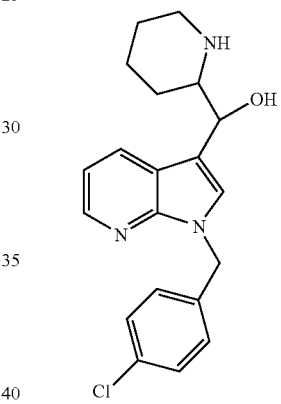

for which an anti-malaria effect was determined.

In the patent U.S. Pat. No. 650,223 (Sterling Drug Inc.), the synthesis of various 2-(imidazolin-2-yl)-alkyl-7-azaindoles or 3-(imidazolin-2-yl)-alkyl-7-azaindoles from the corresponding 2- or 3-cyanoalkyl-7-azaindoles is described and the use of these compounds as vasoconstrictors is claimed.

7-azaindoles have not previously been known as inhibitors of PDE 4.

DESCRIPTION OF THE INVENTION

The invention relates to substituted 7-azaindoles of the general formula

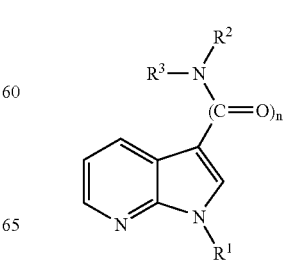

in which n can be 1 or 2 and $R^1$ represents a —$C_1$ to —$C_{10}$ linear or branched alkyl group, optionally substituted one or more times with —OH, —SH, —$NH_2$, —$NHC_1$ to —$NHC_6$ alkyl, —$N(C_1$ to $C_6$-alkyl$)_2$, —$NHC_6$ to —$NHC_{14}$ aryl, —$N(C_6$ to $C_{14}$ aryl$)_2$, —$N(C_1$ to $C_6$ alkyl)($C_6$ to $C_{14}$ aryl), —$NO_2$, —CN, —F, —Cl, —Br, —I, —O—$C_1$ to —O—$C_6$ alkyl, —O—$C_6$ to —O—$C_{14}$ aryl, —S—$C_1$ to —S—$C_6$ alkyl, —S—$C_6$ to —S—$C_{14}$ aryl, —$SO_3H$, —$SO_2C_1$ to —$SO_2C_6$ alkyl, —$SO_2C_6$ to —$SO_2C_{14}$ aryl, —$OSO_2C_1$ to —$OSO_2C_6$ alkyl, —$OSO_2C_6$ to —$OSO_2C_{14}$ aryl, —COOH, —(CO)$C_1$ to —(CO)$C_5$ alkyl, with mono-, bi- or tricyclic, saturated or monounsaturated or multi-unsaturated carbocyclic compounds with 3 to 14 ring elements, with mono-, bi-or tricyclic saturated or monounsaturated or multi-unsaturated heterocyclic groups with 5 to 15 ring elements and 1 to 6 hetero atoms, which preferably are N, O and S, the $C_6$ to $C_{14}$ aryl groups and the carbocyclic and heterocyclic substituents, in turn, possibly may be monosubstituted or multi-substituted with $R^4$, —$C_2$ to $C_{10}$ alkenyl, monounsaturated or multi-unsaturated, linear or branched, optionally monosubstituted or multi-substituted with —OH, —SH, —$NH_2$, —$NHC_1$ to —$NHC_6$ alkyl, —$N(C_1$ to $C_6$-alkyl$)_2$, —$NHC_6$ to —$NHC_{14}$ aryl, —$N(C_6$ to $C_{14}$ aryl$)_2$, —$N(C_1$ to $C_6$ alkyl)($C_6$ to $C_{14}$ aryl), —$NO_2$, —CN, —F, —Cl, —Br, —I, —O—$C_1$ to —O—$C_6$ alkyl, —O—$C_6$ to —O—$C_{14}$ aryl, —S—$C_1$ to —S—$C_6$ alkyl, —S—$C_6$ to —S—$C_{14}$ aryl, —$SO_3H$, —$SO_2C_1$ to —$SO_2C_6$ alkyl, —$SO_2C_6$ to —$SO_2C_{14}$ aryl, —$OSO_2C_1$ to —$OSO_2C_6$ alkyl, —$OSO_2C_6$ to —$OSO_2C_{14}$ aryl, —COOH, —(CO)$C_1$ to —(CO)$C_5$ alkyl, with mono-, bi- or tricyclic, saturated or monounsaturated or multi-unsaturated carbocyclic compounds with 3 to 14 ring elements, with mono-, bi-or tricyclic saturated or monounsaturated or multi-unsaturated heterocyclic groups with 5 to 15 ring elements and 1 to 6 hetero atoms, which preferably are N, O and S, the $C_6$ to $C_{14}$ aryl groups and the carbocyclic and heterocyclic substituents, in turn, possibly may be monosubstituted or multi-substituted with $R^4$, $R^2$ and $R^3$ may be the same or different, only one of the two representing hydrogen, and furthermore, $R^2$ and $R^3$ can represent —$C_1$-$C_5$ alkyl, optionally monosubstituted or multi-substituted with —OH, —SH, —$NH_2$, —$NHC_1$ to —$NHC_6$ alkyl, —$N(C_1$ to $C_6$-alkyl$)_2$, —$NO_2$, —CN, —F, —Cl, —Br—, —I, —O—$C_1$ to —O—$C_6$ alkyl, —S—$C_1$ to —S—$C_6$ alkyl-phenyl, -pyridyl -phenyl, optionally monosubstituted or multi-substituted with —OH, —SH, —$NH_2$, —$NHC_1$ to —$NHC_3$ alkyl, —$N(C_1$ to $C_3$-alkyl$)_2$, —$NO_2$, —CN, —COOH, —$COOC_1$ to —$COOC_3$ alkyl, —F, —Cl, —Br—, —O—$C_1$ to —O—$C_3$ alkyl, —S—$C_1$ to —S—$C_3$ alkyl -pyridyl, optionally monosubstituted or multi-substituted with —$NO_2$, —CN, —COOH, —$COOC_1$ to —$COOC_3$ alkyl, —Cl, —Br—, —O—$C_1$ to —O—$C_3$ alkyl, —S—$C_1$ to —S—$C_3$ alkyl, as well as

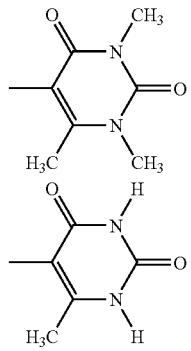 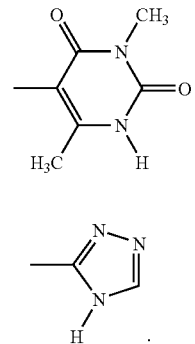

Together, the —$NR^2R^3$ group can represent

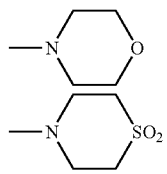 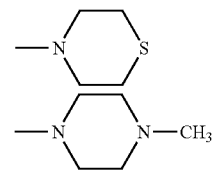

in which $R^4$ represents

—H, —OH, —SH, —$NH_2$, —$NHC_1$ to —$NHC_6$ alkyl, —$N(C_1$ to $C_6$ alkyl$)_2$, $NHC_6$ to $NHC_{14}$ aryl, $N(C_6$ to $C_{14}$ aryl$)_2$, —$N(C_1$ to $C_6$ alkyl)($C_6$ to $C_{14}$ aryl), —$NHCOC_1$ to —$NHCOC_6$ alkyl, —$NO_2$, —CN, —COOH, —$COOC_1$ to —$COOC_6$ alkyl, —(CO)$C_1$ to —(CO)$C_6$ alkyl, —(CS)$C_1$ to —(CS)$C_6$ alkyl, —F, —Cl, —Br, —I, —O—$C_1$ to —O—$C_6$ alkyl, —O—$C_6$ to —O—$C_{14}$ aryl, —S—$C_1$ to —S—$C_6$ alkyl, —S—$C_6$ to —S—$C_{14}$ aryl, —$SOC_1$ to —$SOC_6$ alkyl, —$SO_2C_1$ to —$SO_2C_6$ alkyl.

In the inventive 7-azaindoles of formula 1 residue $R^1$ preferably is a $C_1$ to $C_{10}$ alkyl residue. Such residue can be linear, branched or cyclic, and preferably is linear. Especially preferred are alkyl residues having 1 to 6, even more preferred having 1 to 4 carbon atoms. In a further preferred embodiment $R^1$ is a $C_2$ to $C_{10}$ alkenyl residue, preferably a $C_2$ to $C_6$, and most preferred a $C_2$ to $C_4$ alkenyl residue. The alkenyl residue can be mono- or multi-unsaturated, for example, di-unsaturated or triply unsaturated. The alkenyl residue can be a linear, branched or cyclic hydrocarbon residue. Especially preferred are residues $R^1$, wherein the alkyl or alkenyl residue is mono- or multi-substituted, for example, disubstituted, trisubstituted, tetrasubstituted or pentasubstituted. In an especially preferred embodiment the residue $R^1$ is a substituted $C_1$ alkyl (i.e. methyl) residue. Among the above-given substituents of the alkyl or alkenyl group of residue $R^1$ substituents —OH, —F, —Cl, —Br, —I, —$C_1$ to $C_4$ alkoxy are particularly preferred. Furthermore, substituents are preferred, wherein an optionally present alkyl residue has 1 to 4 carbon atoms and an optionally present aryl residue has 6 to 10 carbon atoms. Among the carbocycles, the phenyl residue is preferred, especially a substituted phenyl residue which is preferably substituted with —F, —Cl, —Br, —I, $C_1$ to $C_6$ alkoxy or hydroxy. Among the heterocycles those are preferred, which have at least one heteroatom selected from N, O or S. Particularly preferred among the heterocycles is the pyridyl residue as well as the isoxazole residue, especially the 3,5-dimethyl isooxazole residue. An example of a condensed carboxylic substituent is the naphthyl residue.

In a particularly preferred embodiment $R^1$ is a group comprising a cyclic hydrocarbon residue, such as cyclopropyl methyl, a linear hydrocarbon, such as n-hexyl, a linear hydrocarbon substituted with an alkoxy residue, such as 2-methoxyethyl, a branched hycdrocarbon residue, such as isobutyl, an unsaturated hydrocarbon residue, such as 2-methylpropene-3-yl or a hydrocarbon residue containing an aromatic group, which residue optionally may be substituted, such as 4-fluorobenzyl, 3-methoxybenzyl, 4-methoxybenzyl, 4-chlorobenzyl, 4-methylbenzyl, 3-hydroxybenzyl or 4-hydroxybenzyl, a group containing a heteroaromatic hydrocarbon, such as 4-pyridylmethyl or 3,5-dimethylisoxaxole-4-methyl or a group containing a condensed aromatic hydrocarbon, such as 1-naphthylmethyl.

In a preferred embodiment, the substituents on the nitrogen atom, $R^2$ and $R^3$ can be an optionally substituted $C_1$ to $C_5$ alkyl residue, preferably a $C_1$ to $C_3$ and particularly preferred a $C_1$ (i.e. methyl) alkyl residue.

One of residues $R^2$ or/and $R^3$ preferably represents a residue comprising a heteroaromatic hydrocarbon, such as 4-pyridylmethyl, whereby said heteroaromatic hydrocarbon further can be substituted, preferably with a halogen, such as 3,5-dichloro-4-pyridyl. In another preferred embodiment $R^2$ or/and $R^3$ is the residue morpholino. Further preferred are residues $R^2$ and $R^3$ comprising an aromatic hydrocarbon which preferably is substituted, in particular, with halogen or carboxy, such as 2,6-dichlorophenyl, 4-carboxyphenyl, 4-ethoxycarbonyl phenyl, 3,4-dimethoxyphenyl. In a further preferred embodiment both $R^2$ and $R^3$ are methoxyethyl. In another preferred embodiment $R^2$ or $R^3$ represents a residue

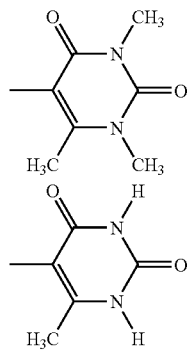
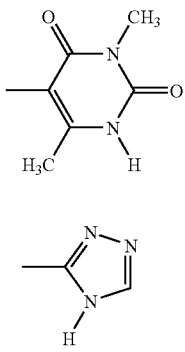

or the group —NR²R³ together represents

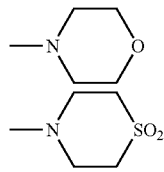
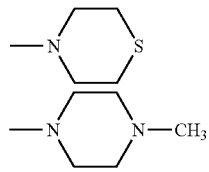

Furthermore, the invention relates to the physiologically tolerated salts of the compounds of formula 1.

The physiologically tolerated salts are obtained in the usual manner by neutralizing the bases with inorganic or organics acids or by neutralizing the acids with inorganic or organic bases. As inorganic acids, hydrochloric acid, sulfuric acid, phosphoric acid or hydrobromic acid, as organic acids, for example, carboxylic, sulfo or sulfonic acid, such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, malic acid, salicylic acid, 3-aminosalicylic acid, ascorbic acid, embonic acid, nicotinic acid, isonicotinic acid, oxalic acid, amino acids, methanesulfonic acid, ethanesulfonic acid, 2-hydroxyethanesulfonic acid, ethane-1,2-disulfonic acid, benzenesulfonic acid, 4-methylbenzenesulfonic acid or naphthalene-2-sulfonic acid, come into consideration. As inorganic bases, sodium hydroxide, potassium hydroxide, ammonia and, as organic bases, amines, preferably tertiary amines, such as trimethylamine, triethylamine, pyridine, N,N-dimethylaniline, quinoline, isoquinoline, α-picoline, β-picoline, y-picoline, quinaldine or pyrimidine, for example, come into consideration.

Moreover, the physiologically tolerated salts of the compounds of formula 1 can be obtained by converting derivatives, which contain tertiary amino groups, in a known manner with quaternizing agents into the corresponding quaternary ammonium salts. As quaternizing agents, alkyl halides, such as methyl iodide, ethyl bromide and n-propyl chloride, but also aryl alkyl halides such as benzyl chloride or 2-phenylethyl bromide come into consideration, for example.

Furthermore, of the compounds of formula 1, which have an asymmetric carbon atom, the invention relates to the D form, the L form and D,L mixtures and, in the case of several asymmetric carbon atoms, to the diastereoisomeric forms. Those compounds of formula 1, which contain asymmetric carbon atoms and usually are obtained as racemates, can be separated into the optically active isomers in a known manner, for example, with an optically active acid. It is, however, also possible to use an optically active starting substance from the very start, a correspondingly optically active or diastereoisomeric compound then being obtained as end product.

The inventive compounds were found to have pharmacologically important properties, which can be used therapeutically.

The inventive compounds are inhibitors of the release of TNFα.

These compounds therefore can be used to inhibit the release of TNFα.

It is therefore an object of this invention that the compounds of formula 1 and their salts, as well as pharmaceutical preparations, which contain these compounds or their salts, can be used for the treatment of illnesses, for which an inhibition of TNFα is useful.

These illnesses include, for example, inflammation of the joints, including arthritis and rheumatoid arthritis, as well as other arthritic illnesses such as rheumatoid spondylitis and osteoarthritis. Further application possibilities are the treatment of patients, who are suffering from osteoporosis, sepsis, septic shock, gram negative sepsis, toxic shock syndrome, respiratory distress syndrome, asthma or other chronic pulmonary diseases, bone resorption diseases or transplant rejection reactions or other autoimmune diseases, such as lupus erythematosus, multiple sclerosis, glomerulonephritis and uveitis, insulin-dependent diabetes mellitus and chronic demyelination.

In addition, the inventive compounds can also be used for the treatment of infections, such as viral infections and parasite infections, for example, for the treatment of malaria, leishmaniasis, infection-induced fever, infection-induced muscle pain, AIDS and cachexia.

The inventive compounds are inhibitors of phosphodiesterase 4.

The inventive compounds therefore can be used to inhibit phosphodiesterase 4.

It is therefore an object of this invention that the compounds of formula 1 and their salts, as well as pharmaceutical preparations, which contain these compounds or their salts, can be used for the treatment of diseases, for which an inhibition of the phosphodiesterase 4 is useful.

Accordingly, the inventive compounds can be used as bronchodilators and for asthma prophylaxis. The compounds of formula 1 furthermore are inhibitors of the accumulation of eosinophiles as well as of their activity. Accordingly, the inventive compounds can also be used in the case of diseases, in which eosinophiles play a role. These diseases include, for example, inflammatory diseases of the respiratory tract such as bronchial asthma, allergic rhinitis, allergic conjunctivitis, atopic dermatitis, eczema, allergic angiitis, inflammations brought about by eosinophiles such as eosinophilic fasciitis, eosinophilic pneumonia and PIE syndrome (pulmonal infiltration with eosinophilia), urticaria, ulcerative colitis, Crohn's disease and proliferative skin diseases such as psoriasis and keratosis.

It is an object of this invention that the compounds of formula 1 and their salts can inhibit the release of TNFα in vitro as well as the LPS-induced pulmonary neutrophil infiltrations in rats in vivo. The entirety of these pharmacologically important properties found confirms that these compounds of formula 1 and their salts, as well as pharmaceutical preparations, which contain these compounds or their salts, can be used therapeutically for the treatment of chronic obstructive lung diseases.

Furthermore, the inventive compounds have neuroprotective properties and can be used for the treatment of diseases, for which neuroprotection is useful. Such diseases are, for example, senile dementia (Alzheimer's disease), loss of memory, Parkinson's disease, depressions, strokes and intermittent claudication.

Further possible applications of the inventive compounds are for the prophylaxis and treatment of prostate diseases, such as benign prostate hyperplasia, pollakisuria, nocturia as well as the treatment of incontinence, colics initiated by urinary calculus and of male and female sexual dysfunctions.

Finally, the inventive compounds can also be used for the inhibition of the development of a medicinal drug dependence upon repeated use of analgesics, such as morphine, as well as for reducing the development of tolerance when these analgesics are used repeatedly.

For the preparation of the medicinal drugs, an effective dose of the inventive compounds or their salts is used in addition to the conventional adjuvants, carriers and additives.

The dosage of active ingredient can vary depending on the way in which it is administered, the age, the weight of the patient, the nature and severity of the diseases to be treated and similar factors.

The daily dose can be administered as a single dose, which is taken once, or divided into two or more doses per day and usually amounts to 0.001 to 100 mg.

Oral, parenteral, intravenous, transdermal, topical, inhalative and intranasal preparations are preferred application forms.

The usual pharmaceutical forms of preparation, such as tablets, coated tablets, capsules, dispersible powders, granulates, aqueous solutions, aqueous or oily suspensions, syrup, liquors or drops may be used.

Solid forms of medicinal drugs may contain inert components and carriers, such as calcium carbonate, calcium phosphate, sodium phosphate, lactose, starch, mannitol, alginates, gelatins, guar gum, magnesium or aluminum stearate, methylcellulose, talcum, highly disperse silica, silicone oil, higher molecular weight fatty acids (such as stearic acid), gelatins, agar agar, vegetable or animal fats and oils and solid high molecular weight polymers (such as polyethylene glycol); preparations, suitable for oral administration, optionally may contain additional flavorings and/or sweeteners.

Liquid forms of medicinal drugs may be sterilized and/or may optionally contain adjuvants such as preservatives, stabilizers, wetting agents, penetrants, emulsifiers, spreading agents, solubilizers, salts, sugars or sugar alcohols to control the osmotic pressure or for buffering purposes and/or viscosity regulators.

Such additives are, for example, tartrate and citrate buffers, ethanol, complexing agents (such as ethylenediaminetetraacetic acid and its nontoxic salts). For controlling the viscosity, high molecular weight polymers come into consideration, such as liquid polyethylene oxide, microcrystalline celluloses such as carboxymethylcelluloses, polyvinylpyrrolidones, dextrans or gelatins. Solid carrier materials are, for example, starch, lactose, mannitol, methylcellulose, talcum, highly disperse silicas, higher molecular weight fatty acids (such as stearic acid), gelatins, agar agar, calcium phosphate, magnesium stearate, animal and vegetable fats, and solid, high molecular weight polymers, such as polyethylene glycol.

Oily suspensions for parenteral or topical applications may contain vegetable, synthetic or semisynthetic oils, such as liquid fatty esters with in each case 8 to 22 carbon atoms in the fatty acid chains such as palmitic, lauric, tridecyl, margaric, stearic, arachidic, myristic, behenic, pentadecyl, linoleic, elaidic, brasidic, erucic or oleic acid, esterified with monohydric to trihydric alcohols with 1 to 6 carbon atoms, such as methanol, ethanol, propanol, butanol, pentanol or their isomers, glycol or glycerol. Such fatty esters are, for example, conventional commercial miglyols, isopropyl myristate, isopropyl palmitate, isopropyl stearate, PEG 6-capric acid, caprylic/capric esters of saturated fatty alcohols, polyoxyethylene glycerol trioleate, ethyl oleate, waxy fatty esters such as synthetic duck rump gland fat, isopropyl esters of coconut oil fatty acids, oleyl oleate, decyl oleate, ethyl lactate, dibutyl phthalate, diisopropyl adipate, fatty acid esters of polyols, etc. Equally suitable are silicone oils of different viscosities or fatty alcohols such as isotridecyl alcohol, 2-octyldodecanol, cetyl stearyl alcohol or oleyl alcohol, fatty acids such as oleic acid. Furthermore, vegetable oils such as castor oral, almond oil, olive oil, sesame oil, cottonseed oil, peanut oil or soybean oil can be used.

As solvent, gel-forming agents and solubilizers, water or solvents miscible with water come into consideration. For example, alcohols, such as ethanol or isopropanol, benzyl alcohol, 2-octyldodecanol, polyethylene glycols, phthalates, adipates, propylene glycol, glycerin, dipropylene glycol, tripropylene glycol, waxes, methyl cellosolve, cellosolve, esters, morpholines, dioxan, dimethylsulfoxide, dimethylformamide, tetrahydrofuran, cyclohexanone, etc. come into consideration As film-forming agents, cellulose ethers can be used, which can dissolve or swell in water as well as in organic solvents, such as hydroxypropylmethylcellulose, methylcellulose, ethylcellulose or soluble starches.

Mixed forms between gel-forming and film-forming agents are also possible. Above all, ionic macromolecules are used here, such as sodium carboxy-methylcellulose, polyacrylic acid, polymethacrylic acid and their salts, sodium amylopectin semiglycolate, alginic acid or propylene glycol alginate as the sodium salt, gum arabic, xanthan gum, guar gum or carrageen gum can be used.

As further formulation aids, the following can be used: glycerin, paraffin of different viscosities, triethanolamine, collagen, allantoin, novantisol acid. The use of surfactants, emulsifiers or wetting agents, such as sodium lauryl sulfate, fatty alcohol ether sulfates, disodium N-lauryl-β-imino dipropionate, polyethoxylated castor oil or sorbitan monooleate, sorbitan monostearate, polysorbates (such as Tween), cetyl alcohol, lecithin, glycerin monostearate, polyoxyethylene stearate, alkylphenol polyglycol ether, cetyltrimethylammonium chloride or monoalkyl or dialkyl polyglycol ether orthophosphoric monoethanolamine salts. Stabilizers such as montmorillonite or colloidal silica for stabilizing emulsions or for preventing the decomposition of the active substances, such as antioxidants, for example, tocopherols or butylhydroxyanisole, or preservatives such as p-hydroxybenzoate esters, may also be required for preparing the desired formulations.

Preparations for parenteral administration may also exist in separate dosage unit forms, such as ampules or vials. Preferably, solutions of the active ingredient are used, especially aqueous solutions and, above all, isotonic solutions; however, suspensions are also used. These injection forms may be made available as finished preparations or prepared directly before use by mixing the active compound, such as the lyophilisate, optionally with other solid carrier substances, with the desired solvent or suspending agent.

Intranasal preparations may exist as aqueous or oily solutions or as aqueous or oily suspensions. They may also exist as lyophilisates, which are prepared with suitable solvents or suspending agents before use.

The production, filling into containers and sealing of the preparations takes place under the usual antimicrobial and aseptic conditions.

The invention furthermore relates to a method for the preparation of the inventive compounds.

Pursuant to the invention, the compounds of the general formula 1, in which $R^1$, $R^2$, $R^3$ have the meanings given above and n=1

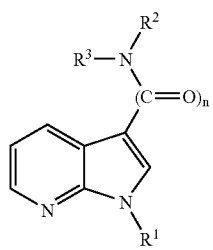

are synthesized in that 7-azaindole-3-carboxylic acids of formula 2, in which $R^1$ has the identical meaning

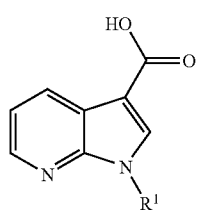

are converted in a known manner with acid chlorides, preferably with thionyl chloride or oxalyl chloride, initially into the analogous 7-azaindole-3-carboxylic acid chlorides of formula 3

Subsequently, the isolated 7-azaindole-3-carboxylic acid chlorides of formula 3 are converted by a reaction with a primary or secondary amine into the inventive compounds of the general formula 1, in which $R^1$, $R^2$, $R^3$ have the meanings given above and n=1. The reaction proceeds advantageously in the presence of an auxiliary base. As auxiliary bases, an excess of the amine, used as reactant, a tertiary amine, preferably pyridine or triethylamine, as well as inorganic bases, preferably alkali hydroxides or alkali hydrides, can be used.

Pursuant to the invention, the compounds of the general formula 1, in which $R^1$, $R^2$, $R^3$ have the meanings given above and n=2

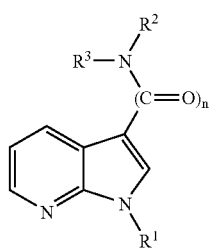

are synthesized in that 7-azaindoles of formula 4, in which $R^1$ has the identical meaning

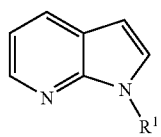

are converted in a known manner by acylating with oxalyl chloride initially into the analogous 7-azaindole-3-yl-glyoxylic acid chlorides of formula 5.

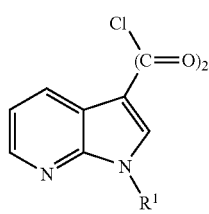

Subsequently, from the 7-azaindole-3-yl-glyoxylic acid chlorides of formula 5, the inventive compounds of the general formula 1, in which $R^1$, $R^2$, $R^3$ have the meanings given above and n=2, are formed by reaction with a primary or secondary amine. The reaction proceeds advantageously in the presence of an auxiliary base. As auxiliary bases, an excess of the amine, used as reactant, a tertiary amine, preferably pyridine or triethylamine, as well as inorganic bases, preferably alkali hydroxides or alkali hydrides, can be used.

EXAMPLES

Examples of Methods for Synthesizing Inventive Compounds of Formula 1 with n=1

Example 1

N-(4-Pyridylmethyl)-1-cyclopropylmethyl-7-azaindole-3-carboxylic Acid Amide

1-Cyclopropylmethyl-7-azaindole-3-carboxylic acid (1.87 g, 8.6 mmoles) is suspended in 15 mL of dichloromethane. While cooling with water, 1.8 mL of oxalyl chloride (17.4 mmoles) are added. The reaction mixture is stirred for 8 hours during which the 1-cyclopropylmethyl-7-azaindole-3-carboxylic acid chloride crystallizes out. It is isolated and dissolved in 18 ml of tetrahydrofuran (THF).

Sodium hydride (60%, 1.14 g) is suspended in 21 mL of THF. While stirring at about 10° C., a solution of 0.93 g of 4-aminomethylpyridine (8.6 mmoles) in 21 mL of THF is added dropwise. After about 15 minutes, the previously prepared solution of 1-cyclopropylmethyl-7-azaindole-3-carboxylic acid chloride is added dropwise to the reaction mixture. Subsequently, the whole is refluxed for 3 hours. After cooling, the reaction mixture is mixed with 36 mL of ethyl acetate and 36 mL of water. The phases are separated and the organic phase is washed with water. The solvent is distilled off and the residue recrystallized from ethanol.

Yield: 1.3 g (50% of the theoretical)

Melting point: 187°–189° C.

Using the synthesis method given, numerous other compounds of formula 1 with n=1 can be synthesized, of which the following are listed by way of example:

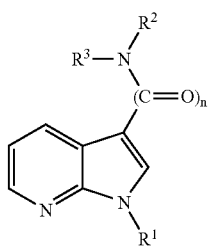

1

| Example | $R^1$ | $-NR^2R^3$ | n | Melting Point [° C.] |
|---|---|---|---|---|
| 1 | cyclopropylmethyl;- | 4-pyridylmethyl-amino- | 1 | 187–189 ethanol |
| 2 | isobutyl- | 3,5-dichloro-4-pyridylamino- | 1 | 168–170 ethanol |
| 3 | n-hexyl- | 3,5-dichloro-4-pyridylamino- | 1 | 136–137 methanol |

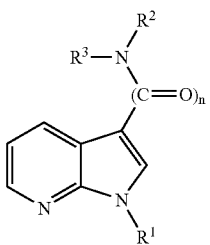

1

| Example | $R^1$ | $-NR^2R^3$ | n | Melting Point [° C.] |
|---|---|---|---|---|
| 4 | cyclopropylmethyl- | 3,5-dichloro-4-pyridylamino- | 1 | 186–187 ethanol |
| 5 | 4-fluorobenzyl | 4-pyridylmethyl-amino- | 1 | 189–191 ethanol |
| 6 | 4-fluorobenzyl- | 3,5-dichloro-4-pyridylamino- | 1 | 232–233 ethanol |
| 7 | 4-methoxy-benzyl- | 3,5-dichloro-4-pyridylamino- | 1 | 193–195 ethanol |
| 8 | 4-chlorobenzyl- | 4-pyridylamino- | 1 | 192–194 methanol |
| 9 | 4-fluorobenzyl- | morpholino- | 1 | 182–184 ethanol |
| 10 | 2-methylpropene-3-yl- | 2,6-dichlorophenyl amino- | 1 | 171–174 ethanol |
| 11 | 4-pyridylmethyl- | 3,5-dichloro-4-pyridylamino- | 1 | 190–192 methanol |

Examples of Methods for Synthesizing Inventive Compounds of Formula 1 with n=2

Example 12

N-(3,5-Dichloropyridine-4-yl)-[1-(3-methoxybenzyl)-7-azaindole-3-yl]-glyoxylic Acid Amide 1-(3-Methoxybenzyl)-7-azaindole (3.57 g, 15 mmoles) is dissolved in 50 mL of t-butyl methyl ether. A solution of 1.54 mL of oxalyl chloride (18 mmoles) in 10 mL of t-butyl methyl ether is added dropwise at 0° C. with stirring. Subsequently, the mixture is refluxed for 2 hours, after which the solvent is distilled off under vacuum. The resulting 1-(3-methoxybenzyl)-7-azaindole-3-yl-glyoxylic acid chloride is obtained as a solid residue, which is suspended in 50 mL of tetrahydrofuran (THF).

To a suspension of 2 g of sodium hydride in 20 mL of THF, 2.4 g of 4-amino-3,5-dichloropyridine (15 mmoles) in 30 mL of THF are added dropwise at −5° C. The mixture is then kept for one hour at 20° C. with stirring. Subsequently, the previously prepared suspension of 1-(3-methoxybenzyl)-7-azaindole-3-yl-glyoxylic acid chloride is added dropwise at about 0° C. Finally, the reaction mixture is refluxed for 4 hours, after which the solvent is removed under vacuum. The residue is stirred with 50 mL of ethyl acetate and 50 mL of water. The phases are separated and the organic phase is washed with water. The solvent is distilled off under vacuum and the residue recrystallized from isopropanol.

Yield: 0.5 g (51.5% of the theoretical)

Melting point: 165°–167° C.

Using the synthesis method given, numerous other compounds of formula 1 with n=2 can be synthesized, of which the following are listed by way of example:

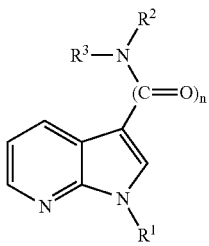

| Example | R¹ | -NR²R³ | n | Melting Point [° C.] |
|---|---|---|---|---|
| 12 | 3-methoxybenzyl- | 3,5-dichloro-4-pyridylamino- | 2 | 165–167 isopropanol |
| 13 | 4-fluorobenzyl- | 4-pyridylamino- x HCl | 2 | 275–278 dec. DMF |
| 14 | 4-fluorobenzyl- | 3,5-dichloro-4-pyridylamino- | 2 | 201–202 ethanol |
| 15 | 4-chlorobenzyl- | 4-pyridylamino- x HCl | 2 | 280–283 dec. DMF |
| 16 | 4-chlorobenzyl- | 3,5-dichloro-4-pyridylamino- | 2 | 205–207 ethanol |
| 17 | 4-methoxybenzyl- | 3,5-dichloro-4-pyridylamino- | 2 | 165–167 ethanol |
| 18 | 4-chlorobenzyl- | 2,6-dichlorophenyl-amino- | 2 | 166–168 ethanol |
| 19 | 4-fluorobenzyl- | 4-carboxy-phenylamino- | 2 | 279–282 isopropanol |
| 20 | 4-fluorobenzyl- | 4-ethoxycarbonyl-phenylamino- | 2 | 209–211 ethanol |
| 21 | 4-fluorobenzyl- | 3,4-dimethoxy-phenylamino- | 2 | 173–176 ethanol |
| 22 | 4-methylbenzyl- | 3,5-dichloro-4-pyridylamino- | 2 | 176–178 ethanol |
| 23 | 4-hydroxybenzyl- | 3,5-dichloro-4-pyridylamino- | 2 | 140–142 ethanol |
| 24 | 3-hydroxybenzyl- | 3,5-dichloro-4-pyridylamino- | 2 | 241–244 ethanol |
| 25 | cyclopropylmethyl- | 3,5-dichloro-4-pyridylamino- | 2 | 215–218 ethanol |
| 26 | n-hexyl- | 3,5-dichloro-4-pyridylamino- | 2 | 165–167 ethanol |
| 27 | isobutyl- | 3,5-dichloro-4-pyridylamino- | 2 | 152–154 methanol |
| 28 | 2-methyl-propene-3-yl- | 3,5-dichloro-4-pyridylamino- | 2 | 114–116 methanol |
| 29 | 2-methoxyethyl- | 3,5-dichloro-4-pyridylamino- | 2 | 166–168 methanol |
| 30 | 1-naphthylmethyl- | 3,5-dichloro-4-pyridylamino- | 2 | 181–183 ethanol |
| 31 | 4-pyridylmethyl- | 3,5-dichloro-4-pyridylamino- | 2 | 199–201 ethanol |
| 32 | 3,5-dimethylisoxazol-4-ylmethyl- | 3,5-dichloro-4-pyridylamino- | 2 | 196–198 ethanol |
| 33 | 4-fluorobenzyl- | —N(C₂H₄—OCH₃)₂ | 2 | 63–66 methanol |
| 34 | 4-fluorobenzyl- | morpholino | 2 | 184–185 ethanol |
| 35 | 4-fluorobenzyl- | thiomorpholine-1,1-dioxide | 2 | 188–191 Ethanol |

-continued

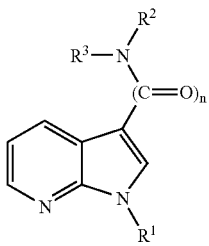

1

| Example | R¹ | -NR²R³ | n | Melting Point [° C.] |
|---|---|---|---|---|
| 36 | 4-fluorobenzyl- | —N(piperazine)N—CH₃ | 2 | 179–181 Methanol |
| 37 | 4-fluorobenzyl- | (pyrimidinedione, H₃C, H, H, N-H) | 2 | 297–300 dec. DMF |
| 38 | 4-fluorobenzyl- | (pyrimidinedione, H₃C, CH₃, H, N-H) | 2 | 310–313 DMF |
| 39 | 4-fluorobenzyl- | (pyrimidinedione, H₃C, CH₃, CH₃, N-H) | 2 | 160–162 acetone |
| 40 | 4-fluorobenzyl- | (triazole, N-H) | 2 | 312–315 dec. DMF |

The inventive compounds are strong inhibitors of phosphodiesterase 4 and of the release of TNFα. The therapeutic potential is confirmed in vivo, for example, by the inhibition of the asthmatic late phase reaction (eosinophilia) as well as by the effect on the allergen-induced vascular permeability of actively sensitized Brown Norway Rats.

Inhibition of Phosphodiesterase

The PDE 4 activity is determined in enzyme preparations from human polymorphonuclear lymphocytes (PMNL) and the PDE 2, 3 and 5 activity is determined with PDE from human thrombocytes. Human blood was anti-coagulated with citrate. By centrifuging at 700×g for 20 minutes at room temperature, the thrombocyte-rich plasma in the supernatant is separated from the erythrocytes and leukocytes. The thrombocytes are lysed by ultrasound and used in the PDE 3 and PDE 5 assays. For the determination of the PDE 2 activity, the cytosolic thrombocyte fraction is purified on an anionic exchange column by means of NaCl gradients and the PDE 2 peak is obtained for the assay. The PMNLs for the PDE 4 determination are isolated by a subsequent dextran sedimentation, followed by a gradient centrifugation with Ficoll-Paque. After the cells have been washed twice, the erythrocytes, still contained, are lysed within 6 minutes at 4° C. by the addition of 10 mL of hypotonic buffer (155 mM of NH₄Cl, 10 mM of NaHCO₃, 0.1 mM of EDTA, pH=7.4). The PMNLs, which are still intact, are washed twice with PBS and lysed with ultrasound. The supernatant of a one-hour centrifugation at 4° C. at 48,000×g contains the cytosolic fraction of the PDE 4 and is used for the PDE 4 measurements.

The phosphodiesterase activity is determined using the method described by Thompson et al. with some modifications (Thompson, W. J. and M. M. Appleman, Assay of cyclic nucleotide phosphodiesterase and resolution of multiple molecular forms of the enzyme, Adv. Cycl. Nucl. Res. 1979, 10, 69–92).

The reaction mixtures contain 50 mM of tris hydrochloride (pH 7.4), 5 mM of magnesium chloride, the inhibitors in various concentrations, the corresponding enzyme preparation as well as the further components necessary for determining the individual isoenzymes (see below). The reaction is started by the addition of the substrate, 0.5 µM of [$^3$H]-cAMP or [$^3$H]-cGMP (approximately 6000 CPM per test). The final volume is 100 ml. Test substances are mixed as stock solutions in DMSO. The DMSO concentration in the reaction mixture is 1% v/v. The PDE activity is not affected by this concentration of DMSO. After the reaction is started by the addition of substrate, samples are incubated for 30 minutes at 37° C. The reaction is stopped by heating the test tubes for 2 minutes at 110° C. The samples remain for a further 10 minutes in ice. The addition of 30 µL of 5'-nucleotidase (1 mg/mL, from a poisonous snake suspension from *Crotalus adamanteus*) is followed by a 10-minutes incubation at 37° C. The samples are stopped on ice, in each case 400 µL of a mixture of Dowex, water and ethanol (1+1+1) is added, mixed well and incubated once again for 15 minutes on ice. The reaction vessels are centrifuged for 20 minutes at 3000×g. Aliquots of the supernatant (200 µL) are transferred directly to scintillation vessels. After the addition of 3 mL of scintillator, the samples are measured in the beta counter.

[$^3$H]-cAMP is used as substrate for the determination of the PDE 4, 3 and 2 activity and [$^3$H]-cGMP is used as substrate for the determination of the PDE 5 activity. The enzyme activities, which are nonspecific in each case, are determined in the presence of 100 µM of Rolipram for the determination of PDE 4 and in the presence of 100 µM of IBMX for the determination of the PDE 3 and 5 and subtracted from the test values. The incubation formulations of the PDE 3 assays contained 10 µM of Rolipram, in order to inhibit possible contaminations by PDE 4. The PDE 2 is tested with an SPA assay of the Amersham Company. The assay is carried out in the presence of the activator of the PDE 2 (5 µM of cGMP).

For the inventive compounds, $IC_{50}$ values ranging from $10^{-9}$ to $10^{-5}$ M were determined for the inhibition of the phosphodiesterase 4. The selectivity towards the PDE types 2, 3 and 5 amounts to a factor of 100 to 10,000.

By way of example, the results of the inhibition of the PDE 4 are summarized in the following Table for selected examples:

| Example | Inhibition of PDE 4 $IC_{50}$ [µmole/L] |
|---------|------------------------------------------|
| 1       | 0.710                                    |
| 2       | 1.400                                    |
| 12      | 0.005                                    |
| 13      | 0.058                                    |
| 14      | 0.004                                    |
| 15      | 0.031                                    |
| 16      | 0.002                                    |
| 17      | 0.008                                    |
| 18      | 0.031                                    |
| 22      | 0.002                                    |
| 23      | 0.001                                    |
| 24      | 0.003                                    |
| 25      | 0.004                                    |
| 26      | 0.021                                    |

-continued

| Example | Inhibition of PDE 4 $IC_{50}$ [µmole/L] |
|---------|------------------------------------------|
| 27      | 0.002                                    |
| 28      | 0.003                                    |
| 32      | 0.113                                    |
| 37      | 0.987                                    |

Inhibition of the Release of TNFα from Cells of Nasal Polyps

The experimental arrangement corresponds essentially to the method described by Campbell, A. M. and J. Bousquet (Anti-allergic activity of $H_1$-blockers, Int. Arch. Allergy Immunol., 1993, 101, 308–310). Nasal polyps form the starting material (material from patients, who had been subjected to a surgical treatment).

The tissue is washed with RPMI 1640 and subsequently digested with protease (2.0 mg/mL), collagenase (1.5 mg/mL), hyaluronidase (0.75 mg/mL), and DNAse (0.05 mg/mL) for two hours at 37° C. (1 g of tissue and 4 mL of RPMI 1640 with enzymes). The cells obtained, a mixture of epithelial cells, monocytes, macrophages, lymphocytes, fibroblasts and granulocytes, are filtered and washed by being centrifuged repeatedly in culture solution and sensitized passively by the addition of human IgE and the cell suspension is brought to a concentration of 2 million cells/mL in RPMI 1640 (supplemented by antibiotics, 10% fetal calf serum, 2 mM of glutamine and 25 mM of Hepes). This suspension is distributed on six-well cell culture plates (1 ml/well). The cells are pre-incubated for 30 minutes with the test substances in different final concentrations and subsequently stimulated to release TNFα by the addition of anti-IgE (7.2 µg/mL). The maximum release into the culture medium takes place after about 18 hours. During this period, the cells are incubated at 37° C. and 5% carbon dioxide. The culture medium (supernatant) is recovered by centrifuging (five minutes at 4000 rpm) and kept at −70° C. until the cytokin is determined. The TNFα in the supernatant is determined with so-called sandwich ELISAs (basic material Pharmingen), with which cytokin concentrations ranging from 30 to 1000 pg/mL can be determined.

Cells, not stimulated with anti IgE, hardly produce any TNFα; on the other hand, stimulated cells secrete large amounts of TNFα, which can be reduced, for example, by PDE 4 inhibitors as a function of the dose. From the percentage inhibition (TNFα release by the cells, stimulated with anti IgE=100%) of the substances tested at different concentrations, the $IC_{50}$ (concentration at 50% inhibition) is calculated.

For the inventive compounds, $IC_{50}$ values ranging from $10^{-7}$ to $10^{-5}$ M are determined.

By way of example, the results of the inhibition of the release of TNFα is summarized for selected examples in the following Table:

| | Inhibition of TNFα Release | |
|---|---|---|
| Example | Concentration | Inhibition [%] |
| 14 | 0.3 µmole/L | 92 |
| 16 | 1.0 µmole/L | 90 |

-continued

| | Inhibition of TNFα Release | |
|---|---|---|
| Example | Concentration | Inhibition [%] |
| 17 | 1.0 µmole/L | 91 |
| 27 | 1.0 µmole/L | 91 |

Inhibition of the Late Phase Eosinophilia 48 Hours After Inhalative Ovalbumin Challenge Using Actively Sensitized Brown Norway Rats The inhibition of pulmonary eosinophilia infiltration by the inventive substances is tested on male Brown Norway Rats (200–250 g), which had been actively sensitized against ovalbumin (OVA). The rats were sensitized by subcutaneous injections of a suspension of 10 µg OVA together with 20 mg of aluminum hydroxide as adjuvant in 0.5 mL of physiological salt solution per animal on days 1, 14 and 21. In addition, the animals at the same time received Bordetella pertussis vaccine dilution injected 0.25 mL i.p. per animal. On the 28th day of the experiment, the animals are placed individually in open 1 L Plexiglas boxes, which are connected to a head-nose exposure device. The animals are exposed to an aerosol of 1.0% ovalbumin suspension (allergen challenge). The ovalbumin aerosol is produced by a nebulizer (Bird Micronebulizer, Palm Springs Calif., USA), which is operated with compressed air (0.2 MPa). The exposure time is one hour, normal controls being nebulized also for one hour with an aerosol of 0.9% salt solution.

Forty-eight hours after the allergen challenge, there is a massive migration of eosinophilic granulocytes into the lungs of the animals. At this time, the animals are anesthetized with an excess of ethyl urethane (1.5 g/kg of body weight i.p.) and a bronchoalveolar lavage (BAL) with 3×4 mL of Hank's balance solution is carried out. The total cell count and the number of eosinophilic granulocytes of the pooled BAL liquid are subsequently determined with an automatic cell differentiation instrument (Bayer Diagnostics Technicon HIE). For each animal, the eosinophiles (EOS) in the BAL are calculated in millions/animal: EOS/µl×BAL recovery (mL)=EOS/animal.

For each test, 2 control groups were run (nebulization with physiological salt solution and nebulization with OVA solution).

The percentage inhibition of the eosinophilia of the experimental group, treated with substance, was calculated according to the following formula:

$$\{((OVAC-SC)-(OVAD-SC))/(OVAC-SC)\}\times 100\% = \% \text{ inhibition}$$

(SC=vehicle-treated control group challenged with 0.9% salt solution; OVAC=vehicle-treated control group challenged with 1% ovalbumin suspension; OVAD=substance-treated experimental group challenged with 1% ovalbumin suspension)

The test substances are applied i.p. or orally as a suspension in 10% polyethylene glycol 300 and 0.5% 5-hydroxyethylcellulose for two hours before the allergen challenge. The control groups are treated with the vehicle in accordance with the application form of the test substance.

The inventive compounds inhibit the late phase eosinophilia after i.p. application of 10 mg/kg by 30% to 100% and, after oral application of 30 mg/kg, by 30% to 75%.

The inventive compounds accordingly are particularly suitable for producing drugs for the treatment of diseases, which are associated with the action of eosinophiles.

By way of example, the results of the inhibition of the eosinophilia for selected examples are summarized in the following Table:

| | Inhibition of Eosinophilia | |
|---|---|---|
| Example | Dose/Application | Inhibition [%] |
| 14 | 10 mg/kg i.p. | 62 |
| | 10 mg/kg p.o. | 59 |
| 16 | 10 mg/kg i.p. | 100 |
| | 10 mg/kg p.o. | 70 |
| 17 | 10 mg/kg i.p. | 75 |
| | 10 mg/kg p.o. | 32 |
| 27 | 10 mg/kg i.p. | 50 |
| | 10 mg/kg p.o. | 70 |

Inhibition of the Lipopolysaccharide (LPS)-Induced Lung Neutrophilia in Lewis Rats The inhibition of pulmonary neutrophil infiltration by the inventive substances is tested on male Lewis Rats (250–350 g). On the day of the experiments, the animals are placed individually in open 1 L Plexiglas boxes, which are connected to a head-nose exposure device. The animals are exposed to an aerosol of a lipopolysaccharide suspension (100 µg LPS/mL of 0.1% hydroxylamine solution) in PBS (LPS provocation). The LPS/hydroxylamine aerosol is nebulized by a nebulizer (Bird Micronebulizer, Palm Springs Calif., USA), which is operated with compressed air (0.2 MPa). The exposure time is 40 minutes, normal controls being nebulized also for 40 minutes with an aerosol of 0.1% hydroxylamine solution in PBS.

Six hours after the LPS provocation, there is a maximum, massive migration of neutrophil granulocytes into the lungs of the animals. At this time, the animals are anesthetized with an excess of ethyl urethane (1.5 g/kg of body weight i.p.) and a bronchoalveolar lavage (BAL) with 3×4 mL of Hank's balance solution is carried out. The total cell count and the number of neutrophil granulocytes of the pooled BAL liquid are subsequently determined with an automatic cell differentiation instrument (Bayer Diagnostics Technicon HIE). For each animal, the neutrophiles (NEUTRO) in the BAL are calculated in millions/animal: NEUTRO/µl×BAL recovery (mL)=NEUTRO/animal.

For each test, 2 control groups were also run (nebulization with 0.1% hydroxylamine solution in PBS and nebulization with 100 µg LPS/mL of 0.1% hydroxylamine solution in PBS).

The percentage inhibition of the neutrophilia of the experimental group, treated with substance, was calculated according to the following formula:

$$\{((LPSC-SC)-(LPSD-SC))/(LPSC-SC)\}\times 100\% = \% \text{ inhibition}$$

SC=vehicle-treated control group challenged with 0.1% hydroxylamine solution; LPSC=vehicle-treated control group challenged with LPS (100 µg/mL 0.1% hydroxylamine solution); LPSD=substance-treated experimental group challenged with LPS (100 µg/mL 0.1% hydroxylamine solution)

The test substances are applied orally as a suspension in 10% polyethylene glycol 300 and 0.5% 5-hydroxyethylcellulose for two hours before the LPS provocation. The control groups are treated with the vehicle in accordance with the application form of the test substance.

The inventive compounds inhibit the neutrophilia after oral application of 1 mg/kg by 40% to 90% and accordingly are particularly suitable for producing drugs for the treatment of diseases, which are associated with the action of neutrophiles.

By way of example, the results of the inhibition of the neutrophilia for selected examples are summarized in the following Table:

| Example | Inhibition of Eosinophilia | |
| --- | --- | --- |
|  | Dose/Application | Inhibition [%] |
| 14 | 1 mg/kg p.o. | 80 |
| 22 | 1 mg/kg p.o. | 64 |
| 27 | 1 mg/kg p.o. | 52 |

What is claimed is:

1. A compound selected from the group consisting of:
N-(4-pyridylmethyl)-1-cyclopropylmethyl-7-azaindole-3-carboxylic acid amide;
N-(3,5-dichloropyridine-4-yl)-1-isobutyl-7-azaindole-3-carboxylic acid amide;
N-(3,5-dichloropyridine-4-yl)-1-hexyl-7-azaindole-3-carboxylic acid amide;
N-(3,5-dichloropyridine-4-yl)-1-cyclopropylmethyl-7-azaindole-3-carboxylic acid amide;
N-(4-pyridylmethyl)-1-(4-fluorobenzyl)-7-azaindole-3-carboxylic acid amide;
N-(3,5-dichloropyridine-4-yl)-1-(4-fluorobenzyl)-7-azaindole-3-carboxylic acid amide;
N-(3,5-dichloropyridine-4-yl)-1-(4-methoxybenzyl)-7-azaindole-3-carboxylic acid amide;
N-(4-pyridylmethyl)-1-(4-chlorobenzyl)-7-azaindole-3-carboxylic acid amide;
1-(4-fluorobenzyl)-7-azaindole-3-carboxylic acid morpholide;
N-(2,6-dichlorophenyl)-1-(2-methylpropene-3-y)-7-azaindole-3-carboxylic acid amide; and
N-(3,5-dichloropyridine-4-yl)-1-(4-pyridylmethyl)-7-azaindole-3-carboxylic acid amide.

2. A compound selected from the group consisting of:
N-(3,5-dichloropyridine-4-yl)-(1-(3-methoxybenzyl)-7-azaindole-3-yl)-glyoxylic acid amide;
N-(4-pyridyl)-(1-(4-fluorobenzyl)-7-azaindole-3-yl)-glyoxylic acid amide hydrochloride;
N-(3,5-dichloropyridine-4-yl)-(1-(4-fluorobenzy l)-7-azaindole-3-yl)-glyoxylic acid amide;
N-(4-pyridyl)-(1-(4-chlorobenzyl)-7-azaindole-3-yl)-glyoxylic acid amide hydrochloride;
N-(3,5-dichloropyridine-4-yl)-(1-(4-chlorobenzyl)-7-azaindole-3-yl)-glyoxylic acid amide;
N-(3,5-dichloropyridine-4-yl)-(1-(4-methoxybenzyl)-7-azaindole-3-yl)-glyoxylic acid amide;
N-(2,6-dichlorophenyl)-(1-(4-chlorobenzyl)-7-azaindole-3-yl)-glyoxylic acid amide;
N-(4-carboxyphenyl)-(1-(4-fluorobenzyl)-7-azaindole-3-yl)-glyoxylic acid amide;
N-(4-ethoxycarbonylphenyl)-(1-(4-fluorobenzyl)-7-azaindole-3-yl)-glyoxylic acid amide;
N-(3,4-dimethoxyphenyl)-(1-(4-fluorobenzyl)-7-azaindole-3-yl)-glyoxylic acid amide;
N-(3,5-dichloropyridine-4-yl)-(1-(4-methylbenzyl)-7-azaindole-3-yl)-glyoxylic acid amide;
N-(3,5-dichloropyridine-4-yl)-(1-(4-hydroxybenzyl)-7-azaindole-3-yl)-glyoxylic acid amide;
N-(3,5-dichloropyridine-4-yl)-(1-(3-hydroxybenzyl)-7-azaindole-3-yl)-glyoxylic acid amide;
N-(3,5-dichloropyridine-4-yl)-(1-cyclopropylmethyl-7-azaindole-3-yl)-glyoxylic acid amide;
N-(3,5-dichloropyridine-4-yl)-(1-hexyl-7-azaindole-3-yl) glyoxylic acid amide;
N-(3,5-dichloropyridine-4-yl)-(1-isobutyl-7-azaindole-3-yl)-glyoxylic acid amide;
N-(3,5-dichloropyridine-4-yl)-(1-(2-methylproperie-3-yl)-7-azaindole-3-yl)glyoxylic acid amide;
N-(3,5-dichloropyridine-4-yl)-(1-(2-methoxyethyl)-7-azaindole-3yl)glyoxylic acid amide;
N-(3,5-dichloropyridine-4-yl)-(1-(1-naphthylmethyl)-7-azaindole-3-yl)-glyoxylic acid amide;
N-(3,5-dichloropyndine-4-yl)-(1-(4-pyridylmethyl)-7-azaindole-3-yl)glyoxylic acid amide;
N-(3,5-dichloropyridine-4-yl)-(1-(3,5-dimethylisoxazole-4-ylmethyl)-7-azaindole-3-yl) glyoxylic acid amide;
N,N-bis(2-methoxyethyl)-(1-(4-fluorobenzyl)-7-azaindole-3-yl)-glyoxylic acid amide;
(1-(4-fluorobenzyl)-7-azaindole-3-yl)-glyoxylic acid morpholide;
(1-(4-fluorobenzyl)-7-azaindole-3-yl)-glyoxylic acid (S,S-dioxo-thiomorpholide);
(1-(4-fluorobenzyl)-7-azaindole-3-yl)-glyoxylic acid (4-methylpiperazide);
N-(6-methyluracil-5-yl)-(1-(4-fluorobenzyl)-7-azaindole-3-yl)-glyoxylic acid amide;
N-(3,6-dimethyluracil-5-yl)-(1-(4-fluorobenzyl)-7-azaindole-3-yl)-glyoxylic acid amide;
N-1,3,6-trimethyluracil-5-yl)-(1-(4-fluorobenzyl)-7-azaindole-3-yl)-glyoxylic acid amide;
and
N-1,2,4-4H-triazole-3-yl)-(1-(4-fluorobenzyl)-7-azaindole3-yl)-glyoxylic acid amide.

3. A 7-Azaindole of the formula 1

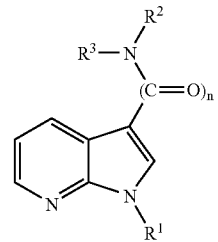

or a physiologically tolerated salt thereof
wherein n is 2;
$R^1$ is a —$C_1$ to —$C_{10}$ linear or branched alkyl; which may be unsubstituted or substituted with at least one of —OH, —SH, —$NH_2$, —$NHC_1$ to $NHC_6$ alkyl, —$N(C_1$ to $C_6$-alkyl$)_2$, —$NHC_6$ to —$NHC_{14}$ aryl, —$N(C_6$ to $C_{14}$ aryl$)_2$, —$N(C_1$ to $C_6$ alkyl)($C_6$ to $C_{14}$ aryl), —$NO_2$, —CN, —F, —Cl, —Br, —I, —O—$C_1$ to —O—$C_6$ alkyl, —O—$C_6$ to —O—$C_{14}$ aryl, —S—$C_1$ to —S—$C_6$ alkyl, —S—$C_6$ to —S—$C_{14}$ aryl, —$SO_3H$, —$SO_2C_1$ to —$SO_2C_6$ alkyl, —$SO_2C_6$ to —$SO_2C_{14}$ aryl, —$OSO_2C_1$ to —$OSO_2C_6$ alkyl, —$OSO_2C_6$ to —$OSO_2C_{14}$ aryl —COOH, —(CO)$C_1$ to —(CO)$C_5$ alkyl, with mono-, bi- or tri-cyclic, saturated or monounsaturated or multi-unsaturated carbocyclic compounds with 3 to 14 ring elements, with mono-, bi- or tricyclic saturated or monounsaturated or multi-unsaturated heterocyclic groups with 5 to 15 ring elements and 1 to 6 hetero atoms selected from the group consisting of N, O and S, or a —$C_2$ to —$C_{10}$ alkenyl, monounsaturated, multiunsaturated, linear, branched, unsubstituted, monosubstituted or multi-substituted with at least one of —OH, —SH, —$NH_2$, to —$NHC_1$ to —$NHC_6$ alkyl, —N($C_1$ to $C_6$-alkyl)$_2$, —$NHC_6$ to —$NHC_{14}$ aryl, —N($C_6$ to $C_{14}$ aryl)$_2$, —N($C_1$ to $C_6$ alkyl)($C_6$ to $C_{14}$ aryl), —$NO_2$, —CN, —F, —Cl, —Br, —I, —O—$C_1$ to —O—$C_6$ alkyl, —O—$C_6$ to —O—$C_{14}$ aryl, —S—$C_1$ to —S—$C_6$ alkyl, —S—$C_6$ to —S—$C_{14}$ aryl, —$SO_3H$, —$SO_2C_1$ to —$SO_2C_6$ alkyl, —$SO_2C_6$ to —$SO_2C_{14}$ aryl, —$OSO_2C_1$ to —$OSO_2C_6$ alkyl, —$OSO_2C_6$ to —$OSO_2C_{14}$ aryl, —COOH, —(CO)$C_1$ to —(CO)$C_5$ alkyl, with mono-, bi- or tri-cyclic, saturated or monounsaturated or multi-unsaturated carbocyclic compounds with 3 to 14 ring elements, with mono-, bi- or tri-cyclic saturated or monounsaturated or multi-unsaturated heterocyclic groups with 5 to 15 ring elements and 1 to 6 hetero atoms selected from N, O and S, wherein said $C_6$ to $C_{14}$ aryl groups and the carbocyclic and heterocyclic substituents may optionally be substituted at least once with $R^4$;

$R^2$ and $R^3$ are independently selected from the group consisting of —H, —$C_1$-$C_5$ alkyl, unsubstituted or monosubstituted or multi-substituted with —OH, —SH, —$NH_2$, —$NHC_1$ to —$NHC_6$ alkyl, —N($C_1$ to $C_3$-alkyl)$_2$, —$NO_2$, —CN, —F, —Cl, —Br—, —I, —O—$C_1$ to —O—$C_6$ alkyl, —S—$C_1$ to —S—$C_6$ alkyl, -phenyl, -pyridyl, or -phenyl, unsubstituted or monosubstituted or multi-substituted with —OH, —SH, $NH_2$, —$NHC_1$, to —$NHC_3$ alkyl, —N($C_1$ to $C_3$-alkyl)$_2$, —$NO_2$, —CN, —COOH, to —COO$C_1$- alkyl, —F, —Cl, —Br—, —O $C_1$ to —O—$C_3$ alkyl, —S—$C_1$ to —S—$C_3$ alkyl, or pyridyl, unsubstituted or monosubstituted or multisubstituted with NO2, —$CN_1$—$COOH_1$—COO$C_1$ to —COO$C_3$ alkyl, —$C_1$, —Br, —O—$C_1$ to —O$C_3$ alky, —S—$C_1$ to S—$C_3$ alkyl, or

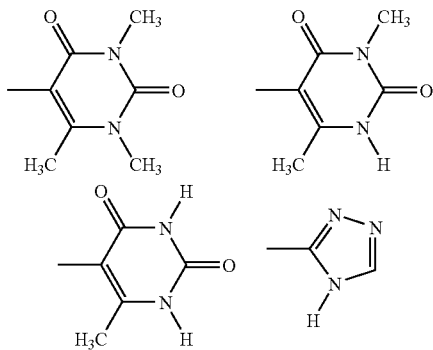

wherein —-$NR^2R^3$ can be

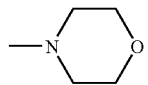 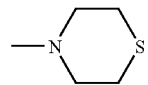

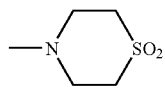 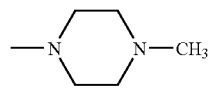

$R^4$ is —H, —OH, —$NH_2$, —$NHC_1$ to —$NHC_6$ alkyl, —N($C_1$ to $C_6$ alkyl)$_2$, —$NCH_6$ to —$NHC_{14}$ aryl, —N($C_6$ to $C_{14}$ aryl)$_2$, —N($C_1$ to $C_6$ alkyl) ($C_6$ to $C_{14}$ aryl), —NHCO$C_1$ to —NHCO$C_6$ alkyl, —$NO_2$, —CH, —COOH, —COO$C_1$ to —COO$C_6$ alkyl, —(CO)$C_1$ to —(CO)$C_6$ alkyl, —(CS)$C_1$ to —(CS)$C_6$ alkyl, —F, —Cl, —Br, —I, —O—$C_1$ to —O—$C_6$ alkyl, —O—$C_6$ to —O—$C_{14}$ aryl, —S—$C_1$ to —S—$C_6$ alkyl, —S—$C_6$ to —S—$C_{14}$ aryl, —SO$C_1$ to SO$C_6$ alkyl, —$SO_2C_1$ to —$SO_2C_6$ alkyl.

4. A physiologically tolerated salt of the 7-azaindole of claim 3, wherein basic substituents of said 7-azaindole are neutralized with inorganic or organic acids or acidic groups are neutralized with inorganic or organic bases or tertiary amines are quatemized to quaternary ammonium salts.

5. A method of preparing the 7-azaindole of claim 3 by reacting 7-azaindole with oxalyl chloride to resultant product is reacted with a primary or secondary amine to form the 7-azaindale, wherein n=2.

6. The method of preparing a 7-azaindole of claim 3 comprising reacting 7-azaindole-3-yl-glyoxylic acid chloride with a primary or secondary amine in the presence of an inorganic base.

7. A method comprising administering a therapeutically effective amount of a 7-azaindole of claim 3 to a subject afflicted with at least one condition selected from the group COPD and asthma to treat the condition by inhibiting phosphodiesterase 4.

8. The method of claim 7, wherein said condition is COPD.

9. The method of claim 7, wherein said condition is asthma.

10. A pharmaceutical composition comprising a 7-azaindole of claim 3 and at least one conventional, physiologically tolerated carrier, diluent or adjuvant.

11. The compound of claim 3 that is N-(3,5-dichloropyridine-4-yl)-[(1-(4-fluorobenzyl)-7-azaindole-3-yl]glyoxylic acid amide.

* * * * *